(12) United States Patent
Petrovic et al.

(10) Patent No.: US 7,089,781 B2
(45) Date of Patent: Aug. 15, 2006

(54) DETECTOR WITH CONDENSER

(75) Inventors: Dragan P. Petrovic, Geneva, IL (US); Lee D. Tice, Bartlett, IL (US)

(73) Assignee: Honeywell International, Inc., Morristown, NJ (US)

( * ) Notice: Subject to any disclaimer, the term of this patent is extended or adjusted under 35 U.S.C. 154(b) by 0 days.

(21) Appl. No.: 10/701,036

(22) Filed: Nov. 4, 2003

(65) Prior Publication Data

US 2005/0092067 A1    May 5, 2005

(51) Int. Cl.
G01N 21/00 (2006.01)
G01N 21/15 (2006.01)
G01N 21/17 (2006.01)
G01N 21/35 (2006.01)

(52) U.S. Cl. .......... 73/31.05; 73/24.02; 73/24.06; 73/31.07; 250/338.5

(58) Field of Classification Search ............. 73/23.2, 73/23.31, 31.05, 31.07, 24.02, 24.06; 250/338.5
See application file for complete search history.

(56) References Cited

U.S. PATENT DOCUMENTS

| | | | | |
|---|---|---|---|---|
| 5,348,562 A | * | 9/1994 | Burrous et al. ............. 96/301 |
| 5,502,308 A | * | 3/1996 | Wong ...................... 250/338.5 |
| 5,811,812 A | * | 9/1998 | Williams et al. ............ 250/343 |
| 5,874,737 A | * | 2/1999 | Bytyn et al. ................ 250/343 |
| 5,879,631 A | * | 3/1999 | Wewers et al. ............... 422/98 |
| 6,019,821 A | | 2/2000 | Hickox |
| 6,151,952 A | * | 11/2000 | Mathews et al. .......... 73/23.31 |
| 6,325,843 B1 | | 12/2001 | Hickox |
| 6,469,303 B1 | * | 10/2002 | Sun et al. .................... 250/343 |
| 6,528,420 B1 | * | 3/2003 | Tong et al. ................. 438/680 |
| 2004/0145485 A1 | * | 7/2004 | Tice .......................... 340/632 |
| 2005/0017206 A1 | | 1/2005 | Tice et al. .................. 250/573 |

FOREIGN PATENT DOCUMENTS

| | | | | |
|---|---|---|---|---|
| GB | 2391622 | * | 2/2004 | ................ 73/31.05 |
| JP | 61-281966 A | * | 12/1986 | ................ 73/23.31 |
| WO | PCT/US97/00840 | | 7/1997 | |

* cited by examiner

Primary Examiner—Daniel S. Larkin
(74) Attorney, Agent, or Firm—Welsh & Katz, Ltd.

(57) ABSTRACT

An ambient condition detector has a housing that carries a sensor of an airborne constituent such as a gas, and a condenser for minimizing an inflow of moisture into the sensor. A filter can be used to reduce fluid flow velocity prior to passing through or by the condenser.

17 Claims, 3 Drawing Sheets

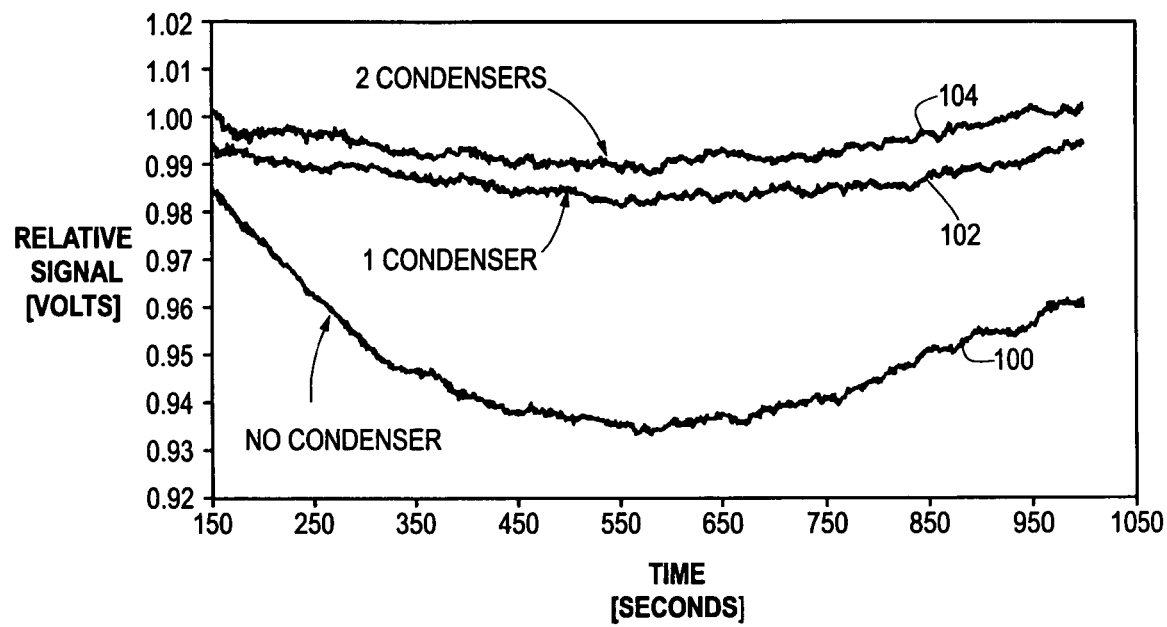

DETECTOR WITH CONDENSER

FIELD OF THE INVENTION

The invention pertains to ambient condition detectors usable in high humidity environments. More particularly, the invention pertains to optical-type gas detectors which remove water vapor from inflowing fluids prior to the fluids entering into a sensing region.

BACKGROUND OF THE INVENTION

Non-dispersive infra-red (NDIR) gas sensors take advantage of selective absorption of radiant energy by specific gases. Analysis of absorption of specific wavelength(s) by a fluid sample provides an indication of the concentration of one or more gases of interest in the sample. The reliability of this process is dependent on the removal or exclusion of water vapor from the sample, including prevention of condensation of water vapor in the sensor.

It has been known to use configurations formed of compressed steel balls in explosion proof gas detectors. The compressed steel balls prevent any gas ignition in the chamber from propagating out to an explosive environment. These types of configurations would inherently provide some dehumidification of gas entering the detector. The dehumidification performance of such a configuration is generally poor since ambient air velocities can provide an unrestricted supply of water vapor to this type of configuration. In these known detectors, gas passes through the configuration of steel balls and into a sensing chamber without first passing through a filter.

One alternate known solution to the problem has been to incorporate an electric heater in the sensor to eliminate condensation of water vapor in the sample. In addition to requiring inclusion of a heater in the sensor, heaters require electrical energy when operating. Heater electrical requirements can become a major problem in systems that include large numbers of dispersed sensors that are powered off of common power and data lines. The power requirements of heaters are also a problem in portable or wearable sensors.

There thus continues to be a need for water vapor excluding, condensation minimizing, sensors that do not require heaters. Preferably, such sensors could be implemented without substantially increasing manufacturing expense or complexity. It would also be preferable if such implementations were compatible with the low weight, low power, low cost requirements of wearable sensors.

BRIEF DESCRIPTION OF THE DRAWINGS

FIG. 6 is a graph illustrating characteristics of different configurations.

DETAILED DESCRIPTION OF THE EMBODIMENTS

Figure 1:
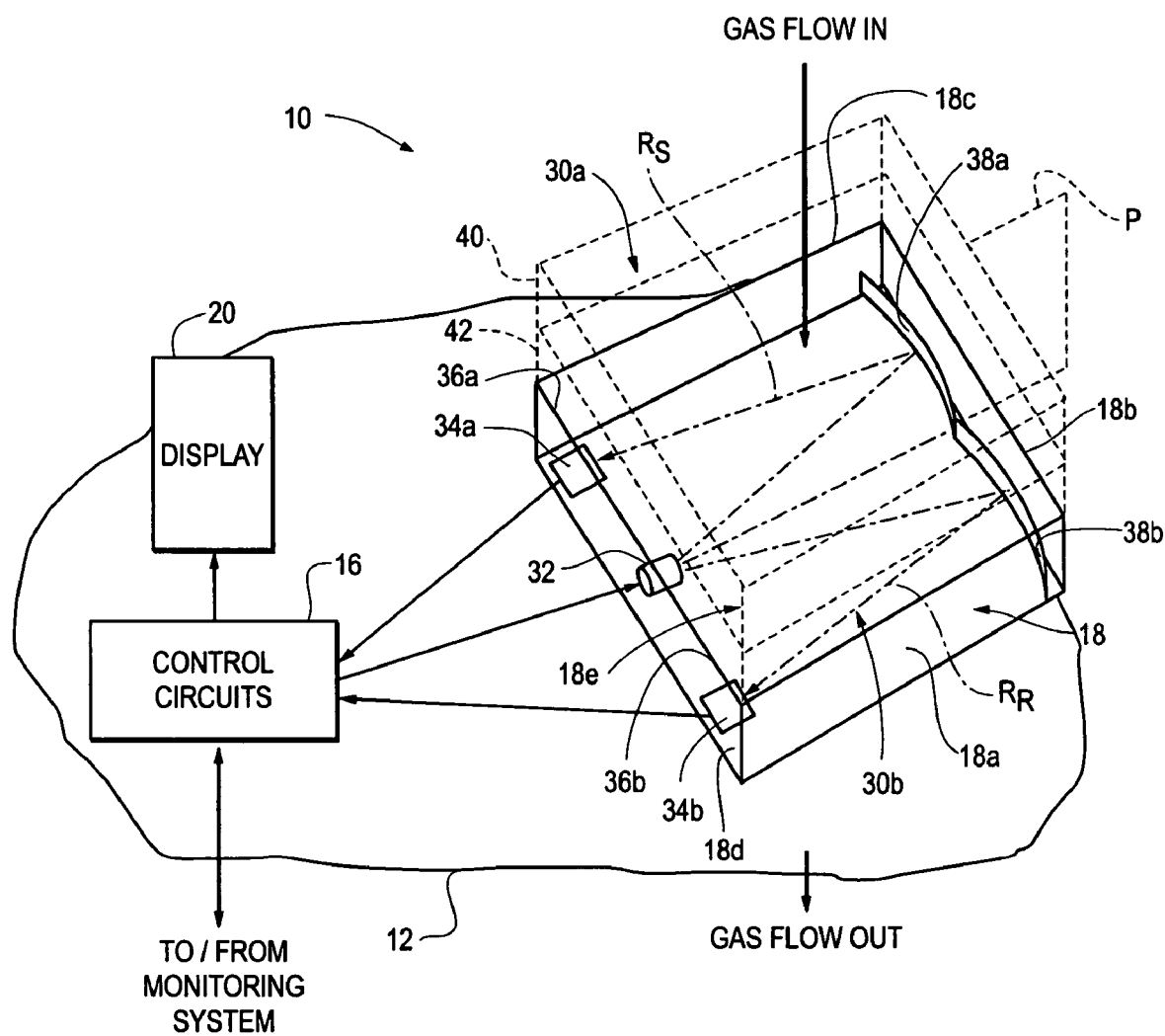
FIG. 1 is a block diagram of a detector in accordance with the invention.

While embodiments of this invention can take many different forms, specific embodiments thereof are shown in the drawings and will be described herein in detail with the understanding that the present disclosure is to be considered as an exemplification of the principles of the invention and is not intended to limit the invention to the specific embodiment illustrated.

In one configuration which embodies the invention, a passive (requires no power) condenser is located between an gas inflow and a sensing chamber of an optical-type (NDIR or the like) gas detector. The condenser has a relatively large mass and large surface area that the gas must pass over prior to entering the sensing chamber.

If the detector is cold enough for condensation to occur within the sensing chamber, the condenser will also be cold and cause the condensation to occur within the condenser. Thus, the condenser will remove the water vapor from the inflowing gas sufficient that the relative humidity of the gas finally entering the sensing chamber is lowered such that it does not reach the dew point within the sensing chamber. If the relative humidity is below the dew point, there will be no condensation in the sensing chamber and the detector will function normally.

The condenser can be implemented with various structures. In one implementation, small steel spheres (or other metal or material of relatively large mass and high thermal conductivity), can be packed close to each other with openings for the gas to pass through. The steel spheres also provide a large surface area upon which condensation can occur to thus lower the relative humidity of the gas passing through it.

Alternately, a condenser can be implemented with plates or other structures that incorporate 1) good heat transfer within the selected material; 2) significant mass to absorb energy from the fluid passing through it, and 3) a large surface area for collecting the water condensed from the fluid.

In yet another configuration, the condenser could be electronic to condense the water from the fluid prior to entry into the sensing chamber of the detector. For example, semi-conduct refrigeration devices could be used to implement a condensation function.

In yet another embodiment, a varying number of filters and a varying number of condensers can be combined in a single detector. For example, one condensing structure can be sandwiched between two filters. A stack of alternating filters and condensers could be located between a fluid or gas inlet and a sensing chamber.

In one preferred embodiment, the condenser can be implemented as a metal plate with inlet openings (slots or holes) for the gas to pass through it. At least one filter is located between the ambient atmosphere and the condenser so that the air velocities at the condenser are reduced.

The primary mode of propagation of the gas and water vapor near or at the condenser is preferably by diffusion after passing through the at least one filter. The filter between the condenser and the ambient atmosphere functions as a barrier controlling the rate at which the water vapor and gas can pass by or through the condenser on their way to the sensing chamber.

The filter(s) and condenser(s) may cause some delay in the gas entering the sensing chamber. However, compensation can be provided for such delays.

FIG. 1 illustrates detector 10 which has a housing 12. Housing 12 carries control circuits 16, which could be implemented in part with a processor and executable instructions. Housing 12 also carries housing 18 for sensing a concentration of a selected gas.

Display 20, driven by signals from control circuit 16 could display gas concentration, for example, parts per million or the like all without limitation. It will be understood that the characteristics of the display 20 are not a limitation of the present invention.

Housing 18 is formed with bounding side walls 18a, b, c, d which bound on interior region 18e. The side walls define a sensing chamber or portion indicated generally at 30a and a reference chamber or portion indicated generally at 30b. In the disclosed embodiment, the sensing and reference chambers 30a, b are open to each other along a common plane P, see FIG. 3.

Plane P corresponds to plane 5—5 and is generally parallel to a direction of flow of gas into/out of detector 10.

Reference chamber 30b is a mirror image of sensing chamber 30a. A shared emitter 32 is located on the common plane P between the sensing and reference portions 30a, b. The housing 18 can be formed of a variety of materials, including cured plastic resin, all without limitation of the present invention.

It will be understood that the configuration of housing 18 is exemplary only. Other sensor configurations come within the spirit and scope of the invention.

Sensors 34a and 34b are carried on side wall 18d. Each of the sensors 34a, b has associated therewith a respective optical filter 36a, b. The filter 36a passes a band of energy associated with the gas to be detected. The filter 36b passes a band of energy not associated with the gas to be detected. Sensors 34a, b and their respective filters 36a, b are symmetrically located relative to plane P and emitter 32.

The filter 36a for the sensing chamber 30a passes a wavelength(s) known to be absorbable by the gas(s) being used. Filter 30b, for reference chamber 30b passes a wavelength(s) not absorbed by the gas(s) being sensed.

Each of the chambers 30a, b also includes a curved concave reflector 38a, 38b. The reflector could be spherical or parabolic all without limitation of the present invention. Other curved surfaces could also be used.

Radiant energy emitted from emitter 32 is equally incident upon reflectors 38a, 38b after passing through the respective sensing chamber 30a or reference chamber 30b. On reflection off of the respective surfaces 38a, b, the radiant energy $R_S$ and $R_R$ passes through respective filter 36a, b and is incident upon respective sensor 3a, b which converts same to a corresponding electrical signal. Those signals are in turn coupled to control circuit 16.

Representative types of gases suitable for being sensed using gas sensor 18 include hydrocarbons, such as carbon monoxide, carbon dioxide, combustible gases, such as methane, ethane and the like as well as water vapor. It will be understood that the gas being sensed is not a limitation of the invention.

Emitter 32 is selected to have a radiant energy output of a wavelength absorbable by the type of gas to be sensed. For example, emitters having wave lengths in the range of three to five microns are suitable for sensing hydrocarbons, such as carbon monoxide or carbon dioxide. Other wave lengths would be used, as would be understood by those of skill in the art, for sensing different gases.

The emitter 32 could be implemented using a light bulb, a light emitting diode, a laser diode or the like all without limitation. It will also be understood that the particular emitter of choice in a given gas sensor is not a limitation of the invention.

Housing 18 is covered, at least in part by a filter 40, for example, a semi-permeable membrane, and an adjacent condenser 42 both illustrated in phantom. Filter 40 excludes undesirable particulate matter and reduces inflow velocity such that movement of gas in housing 18 substantially results from diffusion.

The condenser 42 extracts gas borne water vapor from the inflow by causing it to condense out on the element 42 prior to flowing into either of the chambers 30a, b. It will be understood that a variety of condenser configurations, some examples of which are discussed below, come within the spirit and scope of the invention.

FIGS. 2–5 illustrate various configurations of a gas detector having one or more condensers. Common elements among the detectors of FIGS. 2–5 have been assigned the same identification numeral.

Figure 2:
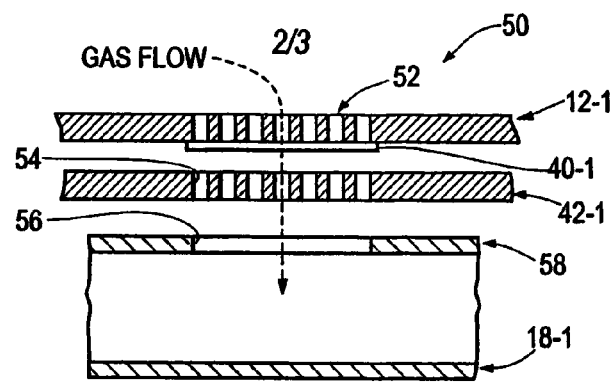
FIG. 2 is an enlarged, partial, side sectional view of one filter/condenser combination.

As illustrated in FIG. 2, a detector 50 defines a plurality of gas inlets 52 in the housing 12-1 having wall(s) 18-1. A gas permeable filter 40-1 permits an inflow of gas from the inlets 52 to pass through a perforated metal condenser 42-1, having openings 54 into a gas sensing chamber 58 via openings 56.

The filter 40-1 functions as a barrier to contamination due to airborne particulate matter, hair, lint and the like. Additionally, it reduces the velocity of the inflowing gas and water vapor as that fluid flows toward condenser 42-1. Water vapor in the gas then liquefies on the condenser 42-1 where temperature of the condenser is below the dew point prior to the gas entering into the sensing chamber 58.

In the detector 50 of FIG. 2, condenser 42-1 carries out two functions:

1. It removes water vapor from the inflowing gas to reduce condensation in the sensing chamber;
2. It cools the gas and remaining water vapor which then enters the sensing chamber 58. As a result, the temperature of the water vapor is closer to the temperature of the sensing chamber 58 thereby making condensation in chamber 58 less likely.

Figure 3:
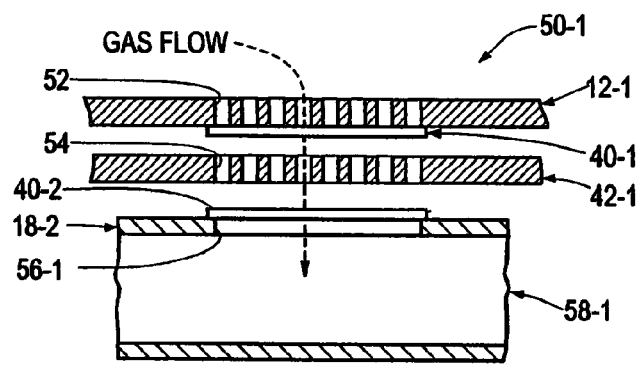
FIG. 3 is an enlarged, partial, side sectional view of an alternate filter/condenser combination.

The detector 50-1 of FIG. 3 incorporates first and second filters 40-1, 40-2. Filter 40-1 is affixed to an interior surface of housing 12-1. Filter 40-2 covers opening 56-1 of gas sensing chamber 58-1. In this instance, the filter 40-1 could be implemented with a material, such as a gas permeable membrane which permits a flow-through of larger molecules than is the case relative to the filter 40-2.

Figure 4:
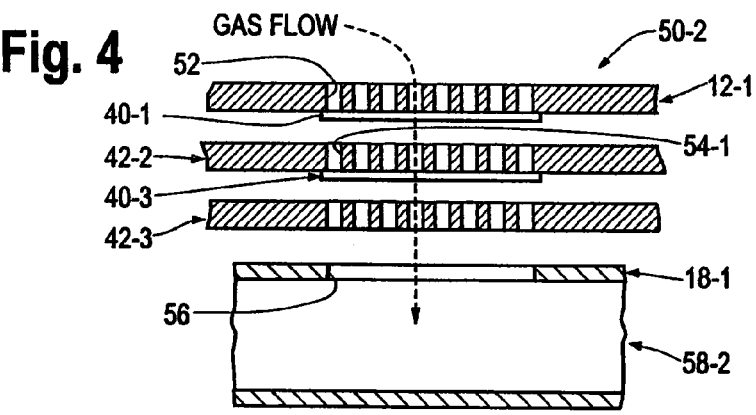
FIG. 4 is an enlarged, partial, side sectional view of another filter/condenser combination.

The detector 50-2 of FIG. 4 incorporates first and second gas permeable filters 40-1, 40-3 which are carried respectively on detector housing 12-1 and first metal condenser 42-2. A second metal condenser 42-3 as carried in detector 50-2 is displaced from the condenser 42-2. Inflowing gas, in detector 50-2, must pass through an alternating stack of permeable filter 40-1, condenser 42-2, (through openings 54-1), permeable filter 40-3 and second condenser 42-3 prior to entering the gas sensing chamber 58-2.

Figure 5:
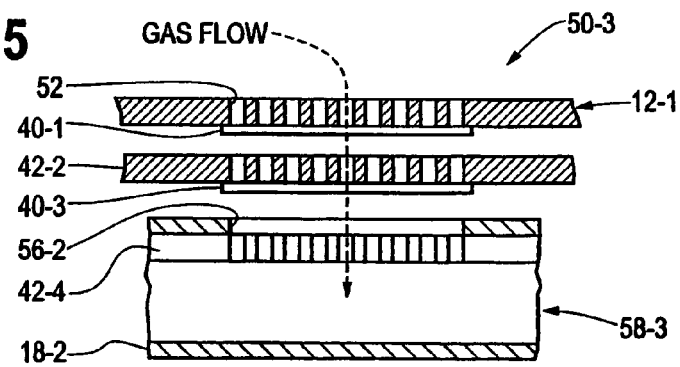
FIG. 5 is an enlarged, partial, side sectional view of yet another filter/condenser combination.

FIG. 5 illustrates detector 50-3 which incorporates first and second gas permeable filters 40-1, 40-3 which are located on opposite sides of condenser 42-2. A second condenser 42-4 is located within housing 18-2 of gas sensing chamber 58-3 having an opening 56-2. It will be understood that the degree of filtering can be altered or selected such that the exterior filter, such as 40-1, performs a coarser filtering function than the interior filter, such as 40-3, which can be selected to pass only smaller molecules of interest. By locating the interior or finer filter 40-3 closer to the sensing chamber, such as 58-1, -2 or -3, the slower diffusion rate in the flowing gas, produced by the finer filter 40-3, for example, will result in minimal delays since the subject filter, 40-3 is closer to the sensing chamber, such as 58-3, than is the case with the exterior, coarser filter, such as 40-1. Hence the gas having the lowest diffusion rate has the shortest distance to diffuse into and throughout the sensing chamber 58-3.

The condenser or condensers, such as 42-2, 42-3, 42-4, can be implemented as singular elements or as composites of multiple elements. Preferred materials include soft metals, such as brass, which is environmentally safe and easily machined or stamped. Other metals having high heat conductivity characteristics can also be used.

It will be understood that the condenser or condensers can be coated not only to prevent corrosion but could also be coated so as to be hydrophilic or hydrophobic without departing from the spirit and scope of the invention. Those of skill will understand that a variety of forms of condensers come within the spirit and scope of the invention provided they remove water vapor from gas entering the detector. Various high thermal conductivity materials could also be used in such condensers, such as metals or high thermal conductivity non-metals.

FIG. 6 illustrates graphs 100, 102 and 104. The graphs 100, 102, 104 illustrate detector output signals plotted against time that the respective detector is being exposed to standardized degrees of humidity. As illustrated in graph 100, where no condenser is present, the output signal or signals from the respective sensor drop off as a function of time due to condensation forming within the sensing chamber. The graph 100 corresponds to a shape also seen, in the absence of humidity, where a gas of interest is diffusing into the sensing chamber. Hence, the presence of the condensing water vapor produces undesirable false positives.

Graph 102 illustrates the improvement over time and detector output where one condenser is present in the respective detector. Finally, graph 104 illustrates further improvement in the presence of two condensers sequentially located in the fluid flow path such that the inflowing fluid must pass through both condensers one after the other prior to diffusing throughout the sensing chamber.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

What is claimed is:

1. A detector comprising:
   a housing;
   a gas sensor carried by the housing, the sensor defining an internal sensing region with at least a first opening for an inflow of gas carrying fluid;
   a first, metal, condenser with second openings therethrough, the condenser is carried in the housing adjacent to the sensor with the first and second openings aligned for a fluid inflow from outside of the housing into the sensing region, the inflow of fluid spreading through the sensing region by diffusion; and
   a membrane filter carried by the housing, the filter overlying at least some of the second openings.

2. A detector as in claim 1 where the filter, condenser and sensing region are arranged in a stacked relationship along a line corresponding to a direction of fluid flow.

3. A detector comprising:
   a housing;
   a gas sensor carried by the housing, the sensor defining an internal sensing region with at least a first opening for an inflow of gas carrying fluid;
   a first, metal, condenser with second openings therethrough, the condenser is carried in the housing adjacent to the sensor with the first and second openings aligned for a fluid inflow from outside of the housing into the sensing region, the inflow of fluid spreading through the sensing region by diffusion;
   a first filter carried by the housing, the filter overlying at least some of the second openings; and
   a second filter, carried by the housing, displaced from the first filter where the filters, the condenser and the sensing region are arranged in a stacked relationship along a line corresponding to a direction of fluid flow.

4. A detector as in claim 3 where one of the filters blocks a flow-through of larger molecules than does the other.

5. A detector as in claim 3 where one filter is located closer to the sensor than is the other filter.

6. A detector as in claim 5 which includes a second, metal, condenser in stacked relationship with the first metal condenser, the second condenser having third openings therethrough.

7. A detector as in claim 6 with the first condenser positioned between the filters.

8. A detector as in claim 6 with one of the condensers positioned between the filters, and where the condensers are spaced apart from one another.

9. A detector comprising:
   at least two perforated, metal condensers with a membrane-type filter therebetween; and
   a gas sensor with at least a gas inflow port, the condensers and filter are located adjacent to the gas sensor so as to provide a gas inflow path through the perforations, the filter and the gas inflow port into the gas sensor.

10. A detector as in claim 9 which includes a second filter with at least one condenser located between the filters.

11. A detector as in claim 10 with the condensers spaced apart from one another.

12. A detector as in claim 11 with one of the condensers located in the gas sensor.

13. A detector as in claim 9 where the condensers, the filter and the sensor are carried by a common housing.

14. A detector as in claim 13 where the housing defines gas inflow openings with an internal gas flow path extending between the gas inflow openings and the sensor.

15. A detector as in claim 14 which includes a gas outflow.

16. A detector comprising:
   a perforated housing;
   at least one perforated metal condenser carried in the housing; and
   a membrane filter that overlies at least some perforations of the housing;
   a gas sensing region in the housing with the at least one perforated metal condenser positioned adjacent thereto, with perforations of the housing, the filter and perforations of the metal condenser forming a fluid inflow path into the gas sensing region.

17. A detector as in claim 16 which includes a second, perforated metal condenser with the filter positioned between the condensers.

* * * * *